United States Patent [19]

Hobbs

[11] Patent Number: 5,183,461
[45] Date of Patent: Feb. 2, 1993

[54] METHOD FOR CLEANING PIERCED EARLOBES

[76] Inventor: Donna M. Hobbs, 14933 Golden Sunset Ct., Poway, Calif. 92064

[21] Appl. No.: 701,830

[22] Filed: May 17, 1991

[51] Int. Cl.⁵ ............................................. A61F 11/00
[52] U.S. Cl. ....................................... 604/49; 604/1; 606/162
[58] Field of Search ................... 606/162, 188, 161; 604/1, 49

[56] References Cited

U.S. PATENT DOCUMENTS

| 4,041,946 | 8/1977 | Barton | 606/188 X |
| 4,497,402 | 2/1985 | Karos | 604/1 X |
| 4,600,008 | 7/1986 | Schmidt | 606/162 |

FOREIGN PATENT DOCUMENTS

| 2557451 | 7/1985 | France | 606/162 |
| 12137 | of 1889 | United Kingdom | 604/1 |
| 264272 | 1/1927 | United Kingdom | 606/162 |

Primary Examiner—Michael H. Thaler
Attorney, Agent, or Firm—Brown, Martin, Haller & McClain

[57] ABSTRACT

A strand of flexible monofilament nylon or nylon-like material which is folded in half so that the two ends meet and are parallel. The ends are bonded by heating and melting the strands to form a single stem from the two strands, the stem having a greater stiffness than the single strand alone. The melting simultaneously creates a rounded tip at the end of the stem. The ends of the strand are joined so that a loop remains open at the fold. The stem is sufficiently stiff so that it can be fed through a pierced ear hole with the rounded end of the stem facilitating feeding the stem through the hole. The loop, which normally is open is compressed as the stem is pulled out the opposite side of the ear. The resilience of the loop is sufficient to permit it to remain slightly expanded so that its greater diameter "scrapes" the ear hole as it passes through. The loop resiles to its original shape as it exits the ear hole.

5 Claims, 1 Drawing Sheet

METHOD FOR CLEANING PIERCED EARLOBES

BACKGROUND OF THE INVENTION

Historically, it has been a common practice to pierce the earlobe so that earrings can be worn. This practice spans all ages, from infants to adults, and both genders. Currently, it is popular to place multiple holes in an earlobe, and even continuing up to the top of the ear, so that many earrings can be worn at one time.

The holes in the earlobes are subject to build-up of residue including dried soap and shampoo, body oils and skin shed by the scar tissue formed around the hole. These residues can collect in the hole and on the earrings facilitating the growth of bacteria which can lead to infection.

Various devices have been described for cleaning or applying medication to pierced ear holes including U.S. Pat. No. 4,041,946 of Barton which discloses a shaft with two ends which snap together to form a ring through the ear hole, the shaft being made of absorbent material to allow medication to be applied to the inside of the ear hole; U.S. Pat. No. 4,497,402 of Karos—a floss-like material inserted through the ear hole to permit the floss, which is soaked with antiseptic solution, to be fed through the ear; U.S. Pat. No. 4,798,216 of McCarty et al. which, similar to Karos, describes a floss impregnated with astringent to be threaded through the pierced ear hole; and U.S. Pat. No. 4,943,274 of Edwards which describes a device in the form of a stud earring in which the shaft is hollow with pores therein through which medication is supplied to the ear hole.

Each of the above-described devices and methods will adequately function to clean or apply medication to the pierced ear hole, however, most are relatively complicated, requiring manufacture and assembly of intricate parts. The McCarty "cleansing floss" is relatively uncomplicated, but it requires the user to pull the floss back and forth to achieve the cleaning which might irritate the ear hole.

It would be desirable to provide a device for cleaning pierced ear holes which is simple and inexpensive to manufacture, and which accomplishes the cleaning in a single motion. It is to such a device that the present invention is directed.

SUMMARY OF THE INVENTION

It is an object of the present invention to provide a simple device for cleaning pierced ear holes which is easy to use.

It is another object of the present invention to provide such a device which is inexpensive and easy to manufacture.

Still another object of the present invention to provide a device which can be used in an alternate embodiment to administer astringent, antibiotic ointment or the like to the pierced ear hole.

In an exemplary embodiment the pierced ear hole cleaner is a strand of flexible monofilament nylon or nylon-like material which is folded in half so that the two ends meet and are parallel. The ends are bonded by heating and melting the strands to form a single stem from the two strands, the stem having a greater stiffness than the single strand alone. The melting simultaneously creates a rounded tip at the end of the stem. The ends of the strand are joined so that a loop remains open at the fold. The stem is sufficiently stiff so that it can be fed through a pierced ear hole with the rounded end of the stem facilitating feeding the stem through the hole. The loop, which normally is open, is compressed as the stem is pulled out the opposite side of the ear. The resilience of the loop is sufficient to permit it to remain slightly expanded so that its greater diameter "scrapes" the ear hole as it passes through. The loop resiles to its original shape as it exits the ear hole.

In an alternate embodiment, the loop portion is wrapped or otherwise covered with an absorbent material such as cotton or other fibrous material which can be either used alone to clean the ear hole or can be soaked in an antiseptic, astringent or antibiotic ointment, for example, for application to the inside of the ear hole.

In still another embodiment, the strand can be made of a tubular woven material, the diameter of which decreases when it is pulled from both ends. In this configuration, the texture of the woven material provides additional scraping, and the increased diameter of the loop portion relative to the shaft diameter, along with the adjustability of that diameter, permits thorough cleaning.

BRIEF DESCRIPTION OF THE DRAWINGS

Understanding of the present invention will be facilitated by consideration of the following detailed description of a preferred embodiment of the present invention, taken in conjunction with the accompanying drawings, in which like reference numerals refer to like parts and in which.

DETAILED DESCRIPTION OF THE PREFERRED EMBODIMENTS

Figure 1:
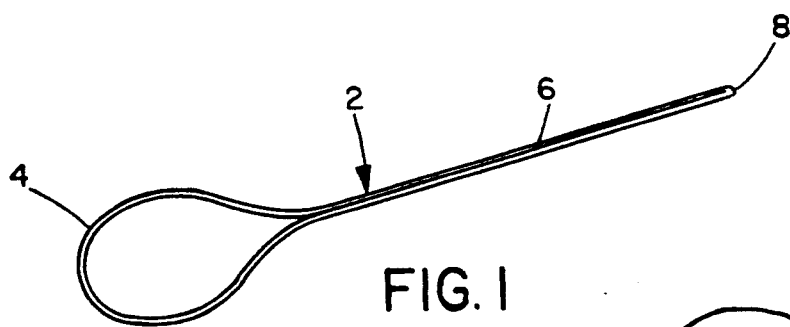
FIG. 1 is a plan view of the cleaner according to the present invention.

Referring to FIG. 1, the pierced ear hole cleaner 2 is constructed of a relatively flexible strand-like or filamentary material such as nylon, polyester, or other similar material. The strand, which is on the order of 6 inches (150 mm) long, is folded in half forming a loop 4 at the midpoint of the strand. Approximately 1.5 inches (38 mm) of the adjacent ends of the strand are bonded together by heating and/or melting the strand so that a single stem 6 is formed. The heating process also causes the stem to become sufficiently liquid that a smooth rounded end 8 is created. The bonding may be accomplished by exposing the strand to, for example, an open flame, a hot iron or an electrical arc welding-type instrument.

Figure 2A:
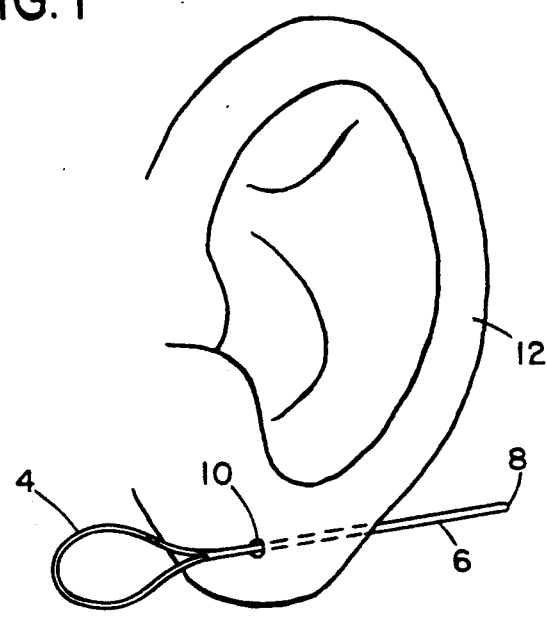
FIG. 2 is a view of the cleaner being inserted into and draws through the ear hole.

The stem 6 is of sufficient thickness that it is stiff enough to insert into the pierced ear hole 10 with relative ease, as illustrated in FIG. 2a. The rounded end 8 facilitates insertion of the stem 6 into the ear hole 10 at the front of the ear 12. The stem 6 is pushed through until it protrudes from the back of the ear where it may be grasped by the user.

Figure 2B:
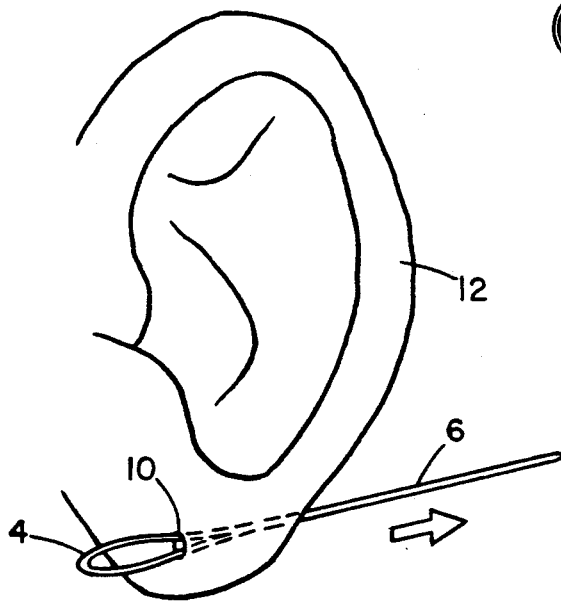

As the stem 6 is pulled out the back of the ear, the loop 4 compresses to pass through the ear hole 10 as shown in FIG. 2b. The resilience of the loop 4 permits it to remain as expanded as possible while still passing comfortably through the ear hole 10, resulting in a gentle scraping of the hole. As the loop 4 exits the back of the ear it resiles to its original shape.

Figure 3:
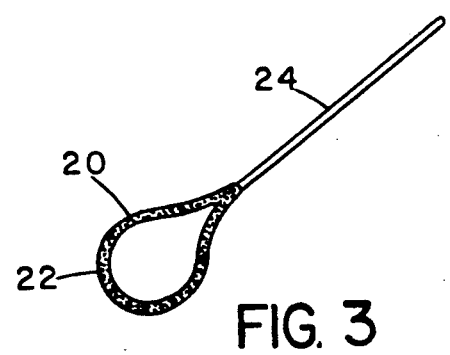
FIG. 3 is a plan view of the second embodiment.

In an alternate embodiment, shown in FIG. 3, the center portion 22 of the strand 20 is coated or covered with a texturized absorbent material, such as cotton or nylon yarn, to permit application of an astringent or antiseptic such as hydrogen peroxide, isopropyl alcohol or Witch Hazel, petroleum jelly or an antibiotic ointment The stem 24 is uncoated to permit it to be bonded in the same manner as above. The coating should be fixed to the strand to prevent it from sliding as the cleaner is used. This coated-type cleaner can be used equally well without a substance applied to it for cleaning purposes alone.

Figure 4:
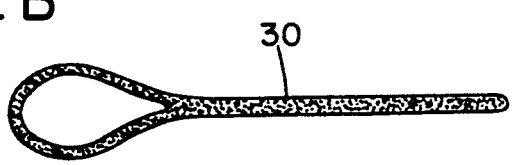
FIG. 4 is a plan view of the third embodiment.

In a third embodiment as shown in FIG. 4, the strand 30 is made from a hollow woven tube which has a diameter comparable to the nylon strand of the preferred embodiment. The woven material can be paper or a similar material which is absorbent and relatively smooth to avoid abrasion. The weave of the strand 30 is such that when it is pulled from both ends its diameter narrows to permit the diameter of the strand to be varied for the amount of cleaning desired.

With the use of the cleaner of the present invention, pierced ear holes can be easily cleaned with a few simple steps. The cleaner is inexpensive to manufacture in its most basic embodiment, can be sold at a low price and, thus, can be disposable after a single use. On the other hand, in the first embodiment it is possible to rinse the cleaner and reuse it if desired because there are no absorbent parts.

It will be evident that there are additional embodiments which are not illustrated above but which are clearly within the scope and spirit of the present invention. The above description and drawings are therefore intended to be exemplary only and the scope of the invention is to be limited solely by the appended claims.

I claim:

1. A method for cleaning a pierced ear hole which comprises:
   selecting a single length of flexible strand having two ends;
   folding said flexible strand back on itself to form a loop portion;
   bonding said two ends together to form an integral stem having a rounded tip and a stiffness greater than that of said flexible strand;
   inserting said stem into and through said pierced ear hole;
   grasping said stem at its tip as it exits said pierced ear hole; and
   pulling said stem so that said loop compresses and passes through said pierced ear hole to clean said pierced ear hole.

2. A method as in claim 1 wherein the step of selecting a single length of flexible strand includes selecting a strand having a coating of texturized absorbent material at its center portion so that said loop portion comprises a coated strand.

3. A method as in claim 2 wherein said coating comprises cotton.

4. A method as in claim 2 further comprising saturating said coating with a substance to be applied to said pierced ear hole.

5. A method as in claim 1 wherein the step of bonding said two ends together comprises exposing said two ends to a heat source causing said two ends to at least partially melt.

* * * * *